United States Patent [19]

Miller

[11] Patent Number: 5,673,861

[45] Date of Patent: Oct. 7, 1997

[54] APPARATUS FOR PROCESSING MEDICAL WASTE

[76] Inventor: Charles Miller, 5406 Rutherglenn Dr., Houston, Tex. 77096

[21] Appl. No.: 649,523

[22] Filed: May 17, 1996

Related U.S. Application Data

[63] Continuation-in-part of Ser. No. 358,923, Dec. 19, 1994, abandoned, which is a continuation-in-part of Ser. No. 238,938, May 6, 1994, abandoned.

[51] Int. Cl.$^6$ .................................................. B02C 18/40
[52] U.S. Cl. .................. 241/69; 241/163; 241/260.1; 241/606
[58] Field of Search .................................. 241/69, 260.1, 241/261, 163, DIG. 38, 606

[56] References Cited

U.S. PATENT DOCUMENTS

| | | | |
|---|---|---|---|
| 2,656,122 | 10/1953 | Borner | 241/260.1 |
| 2,717,742 | 9/1955 | Weigham et al. | 241/260.1 |
| 4,453,676 | 6/1984 | Arnaldo | 241/60 |
| 4,578,185 | 3/1986 | Wilson et al. | 241/606 X |
| 4,884,756 | 12/1989 | Pearson | 241/42 |
| 5,089,228 | 2/1992 | Meijer | 241/606 X |

FOREIGN PATENT DOCUMENTS 3829380  3/1990  Germany .......................... 241/606

*Primary Examiner*—John M. Husar

[57] ABSTRACT

An apparatus for converting unconsolidated medical waste into medical waste residue. A horizontal shaft supports revolving cutter blades having teeth which intermesh with teeth on stationary cutter blades. The rotating shaft forces the medical waste into contact with the cutting region between the revolving and stationary teeth to generate medical waste residue, and blades transport the medical waste residue toward a discharge. A first stage cutter can make an initial cut on the unconsolidated medical waste, and a second stage cutter can further reduce the particle size of the medical waste residue. A disinfectant or sterilant can be introduced into contact with the medical waste to convert infectious waste into nonhazardous medical waste residue.

18 Claims, 3 Drawing Sheets

APPARATUS FOR PROCESSING MEDICAL WASTE

This patent application is a continuation-in-part application of U.S. Ser. No. 08/358,923 filed Dec. 19, 1994, now abandoned, as a continuation-in-part of U.S. Ser. No. 08/238,938 filed May 6, 1994, now abandoned, each entitled "Machine for Volume-Reducing and Sterilizing Infectious and Non-Infectious Medical Waste, the disclosures of which are both incorporated herein by reference in their entirety.

BACKGROUND OF THE INVENTION

The present invention relates to the field of medical waste treatment and disposal. More particularly, the present invention relates to an apparatus for volume reducing unconsolidated medical waste and for processing such medical waste into non-infectious medical waste residue.

Infectious and non-infectious medical waste provides significant disposal problems. Although medical waste is often incinerated, incineration procedures generate toxic fumes, tainted water effluent, and other environmental hazards. Consequently, mechanical and chemical treatment processes have been developed to convert medical waste into a benign waste product that can be safely transported and stored.

The diversity of medical waste components presents unique treatment and processing difficulties. "Medical waste" as used herein includes medical red-bag waste, hypodermic needles, syringes and other sharps, sharps containers, bandages, surgical drapes and wraps, hospital gowns, plastics, paper products, cardboard, metals and other wastes generated by the medical care industry. The shape, size and composition of these materials significantly varies. Shredding and other volume reducing procedures facilitate the treatment, transportation and storage of medical waste. Additionally, the particle size of unconsolidated medical waste is preferably reduced to increase the waste surface area in contact with sterilants.

Conventional shredders typically reduce a single type, homogeneous material and are not effective for shredding materials having different physical characteristics. Various conventional shredders have been developed to shred specific materials. For example, U.S. Pat. No. 2,717,742 to Weigham et al. (1955) disclosed a machine for shredding alkali cellulose. U.S. Pat. No. 3,973,735 to Ito et al. (1976) disclosed a machine combining beaters and a hollow cylindrical screen for processing municipal waste. U.S. Pat. Nos. 5,225,137 to Sadr (1993) and 5,289,978 to Lundquist (1994) disclosed machines and methods for recycling plastic bottles, and U.S. Pat. No. 5,356,054 to Loppoli et al. (1994) disclosed a shredder for cutting and dispensing fodder.

Conventional shredders having the capability to pulverize hypodermic needles and other metal components are ineffective against tightly wound hospital gowns composed of tough fibrous materials compressed into a large bundle. Shredders effective against plastic products are ineffective against hypodermic needles and other metal components. Accordingly, conventional shredders are not readily adaptable to the effective processing of unconsolidated medical waste.

Medical waste processing is complicated by the contamination of medical related products with blood and other biological fluids and tissue infectious to biological organisms. Infectious waste is preferably processed to sterilize or disinfect pathogens in the medical waste before the medical waste is transported and stored. Medical waste can be bombarded with microwaves, bathed in steam, bleach, acid or other disinfectants to sterilize or disinfect the medical waste.

Various systems have been specifically developed to process medical waste into non-infectious medical waste residue. U.S. Pat. No. 4,185,973 to Tester (1980) disclosed a vertical, gravity fed shredder having two contra-rotating cutters for grinding hospital waste. In U.S. Pat. No. 5,054,696 to Mennel et al. (1991), medical waste was fed downwardly with a vertically oriented hydraulic ram, was mechanically shredded with an auger screw, and was fed into a hammermill disintegrator. Similarly, U.S. Pat. No. 4,578,185 to Wilson et al. (1986) disclosed a vertically fed shedder having a hammermill for grinding medical waste.

In other medical waste processing systems, U.S. Pat. No. 4,884,756 to Pearson (1989) disclosed a combination of shredders and augers for cutting and mixing medical waste, and U.S. Pat. No. 5,048,766 to Gaylor et al. (1991) disclosed a series of auger grinders for cutting medical waste. U.S. Pat. No. 5,150,843 to Miller et al. (1992) disclosed a vertically disposed ram for feeding medical waste into opposing cutting heads. U.S. Pat. No. 5,089,228 to Meijer (1992) disclosed a combination of shredding disks and an auger for shredding medical waste. U.S. Pat. No. 5,236,135 to Wilson et al. (1993) disclosed an apparatus having pivotal blades for cutting medical waste. U.S. Pat. No. 5,346,142 disclosed a processing system, U.S. Pat. No. 5,362,443 to Tanaka et al. (1994) disclosed opposing cutter heads for shredding medical waste before the medical waste was processed with steam, and U.S. Pat. No. 5,389,347 to Hall (1995) disclosed a helical blade or combination of blades on a rotating shaft to grind and pulverize medical waste.

These references illustrate state of the art medical waste treatment systems using hammermill cutters, coacting cutter blades, and helical augers to volume reduce medical waste. These known techniques have limitations regarding the grinding effectiveness for unconsolidated medical waste, process flow capabilities, and reliability concerns due to jammed components and other maintenance requirements.

Accordingly, a need exists for an improved apparatus for processing infectious and non-infectious medical waste. The apparatus should efficiently reduce the volume of the medical waste, should be economic to construct and to operate, and should facilitate the conversion of infectious medical waste into non-infectious medical waste residue.

SUMMARY OF THE INVENTION

The present invention provides a unique apparatus for converting unconsolidated medical waste into medical waste residue. The apparatus comprises a housing having an inlet for receiving medical waste and having an interior defined by an interior surface. A rotatable shaft within the housing has a substantially hozizontal axis and is attached to the base of a revolving cutter having a plurality of cutter teeth on a cutter surface radially outward from the shaft. The revolving cutter has a longitudinal axis parallel to the shaft longitudinal axis. A stationary cutter proximate to the housing interior surface includes a plurality of teeth for engagement with the revolving cutter teeth for reducing the medical waste into medical waste residue. An outlet permits the discharge of the medical waste residue from the housing interior, and a propeller moves the medical waste toward the outlet.

In other embodiments of the invention, a disinfectant can be injected into contact with the medical waste during the conversion to medical waste residue. A first stage cutter can initially reduce the medical waste before the medical waste is placed within the housing, and the propeller can comprise a vane positioned on the rotatable shaft.

DESCRIPTION OF THE PREFERRED EMBODIMENTS

The present invention overcomes the shortcomings of prior art systems by providing an efficient apparatus for converting unconsolidated medical waste into medical waste residue. As used herein, the term "medical waste residue" means unconsolidated medical waste that has been, reduced, comminuted or otherwise converted into a selected particle size range smaller than the average component size of the unconsolidated medical waste. Unconsolidated medical waste is reduced to lessen the volume of the medical waste. Additionally, unconsolidated medical waste is reduced into medical waste residue so that a greater surface area of the medical waste particles is exposed to a disinfecting sterilant. Reduction of the medical waste into medical waste residue further converts the medical waste into a homogeneous blend, unidentifiable as to source, rendering the medical waste into a form suitable for landfill disposal.

Figure 1:
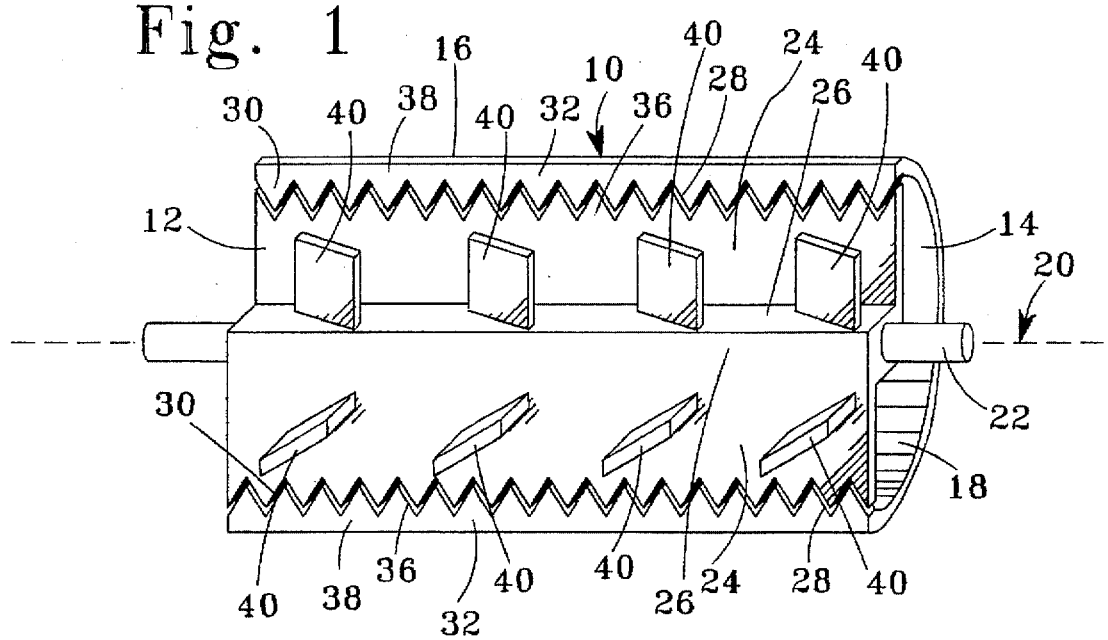
FIG. 1 illustrates a sectional view of a housing and cutter elements for one embodiment of the invention.

FIG. 1 illustrates one embodiment of the invention, wherein housing 10 has inlet 12 and discharge 14. Unconsolidated medical waste can be fed into inlet 12 with a gravity fed hopper, hydraulic press, conveyor, or other technique known in the art. Housing 10 is shown as a generally cylindrical structure having exterior surface 16 and interior surface 18 defining an interior volume. Although the diameter and length of housing 10 are not critical to the successful operation of the invention, the invention permits the efficient processing of medical waste in a relatively small volume when compared to conventional shredders. Housing 10 has longitudinal axis 20 which is preferably horizontal or substantially horizontal for the reasons stated below.

Rotatable shaft 22 is engaged with housing 10 and has a longitudinal axis coincident with longitudinal axis 20 of housing 10 in a preferred embodiment of the invention. Shaft 22 can be turned with an electric motor or other power source (not shown). Shaft 22 can be round or can be shaped as a square shaft for facilitating attachment of revolving cutters 24. At least one revolving cutter 24 has base 26 attached to shaft 22, and has cutting surface 28 extending radially outwardly from shaft 22. Revolving cutter 24 has a longitudinal dimension parallel to the longitudinal axis of shaft 22. A plurality of teeth, generally represented as teeth 30, are formed into or are attached to cutting surface 28.

At least one stationary cutter 32 is positioned proximate to housing interior surface 18 and defines a cutting surface 34 having a plurality of teeth 36. In one embodiment of the invention, stationary cutter 32 can have base 38 welded, bolted or otherwise attached to interior surface 18 as illustrated. In other embodiments of the invention, stationary cutter 32 can be attached to the inlet and discharge ends of housing 10 or in other ways so that stationary cutter 32 is proximate to interior surface 18. Teeth 36 are positioned so that teeth 36 mesh with teeth 30 as revolving cutter 24 revolves relative to stationary cutter 32. This relative movement provides a cutting action on the medical waste which operates to shear and otherwise reduce the medical waste. Teeth 30 and 36 cooperate so that one set of teeth momentarily holds a medical waste particle as the other teeth move relative thereto, thereby stretching and shearing the medical waste particle into incrementally smaller medical waste particles. Beginning at inlet 12, the medical waste is unconsolidated and gradually becomes reduced into medical waste residue.

As teeth 30 and 36 cooperate to reduce the unconsolidated medical waste into medical waste residue, propellers such as impeller blades 40 urge the medical waste residue toward discharge 14. In one embodiment of the invention as illustrated, blades 40 can be welded or otherwise attached to shaft 22 for moving the medical waste residue within the interior of housing 10. Contact between blades 40 during rotation of blades 40 will impact the medical waste residue and will impart energy for transporting the medical waste residue. Conveyor blades, screw threads, or other mechanical forms can be substituted for blades 40. The size, configuration, and orientation of blades 40 will control the movement and flow rate of medical waste residue through housing 10. As shown in FIG. 1, planar blades 40 are oriented at a forty-five degree angle to longitudinal axis 20. If a longer processing time within housing 10 is desired, the angle indicated between blades 40 and longitudinal axis 20 can be decreased. If a higher flow rate of medical waste residue through housing 10 is desired, the angle between blades 40 and longitudinal axis 20 can be increased so that rotation of blades 40 imparts more energy to the medical waste residue in a direction toward discharge 14.

The invention contemplates a single revolving cutter 24 and a single stationary cutter 32 for reducing unconsolidated medical waste. Additional revolving cutters 24 and stationary cutters 32 can be added to modify the cutting performance of the system. For example, a plurality of stationary cutters 32 can be positioned along interior surface 18 to provide additional cuts per unit length of housing 10 as revolving cutter 24 rotates about longitudinal axis 20. A single revolving cutter 24 is useful in reducing bulky unconsolidated waste material. Additional revolving cutters 24 can be useful in providing additional cuts per revolution of shaft 22 in other applications.

The horizontal alignment of housing 10, shaft 22, revolving cutter 24 and stationary cutter 32 provides unique benefits over vertically oriented medical waste shredders. In vertical shredders, gravity pulls the medical waste downwardly as the cutters turn. Accordingly, the heaviest particles such as metals in the medical waste residue are accelerated by gravity at a faster rate than lighter particles, thereby reducing the processing time within the shredder for the heavier particles. This result is undesirable because the heavier particles typically require more processing cuts to successfully reduce the heavier particles to the same degree of reduction achieved for lighter particles in the medical waste residue.

Conversely, the horizontal alignment of housing 10 and the orientation of the cutting elements provides a uniquely different benefit to the processing of medical waste. As shaft 22 and revolving cutter 24 rotate, centrifugal force urges the heavier particles of medical waste residue toward interior surface 18 of housing 10. Because the cutting surfaces between teeth 30 and 36 are positioned proximate to interior surface 18, the heavier particles in the medical waste residue are urged by centrifugal force outwardly toward the cutting surfaces between teeth 30 and 36. This combination causes the heavier particles within the medical waste residue to experience more "cuts" than lighter particles within the medical waste residue. Depending on the number of teeth 30 and 36, the length of revolving cutter 24 and stationary cutter 32, and the number of revolutions of shaft 22, millions of cuts can be made during the time that a certain portion of medical waste is processed between inlet 12 and discharge 14.

The cutting efficiency provided by the invention is increased by positioning the cutting surfaces between teeth 30 and 36 proximate to interior surface 18 of housing 10. By having a single revolving shaft 22, the elements of the present invention cooperate to uniquely furnish an efficient cutting action with minimal energy consumption. The centrifugal force imparted by revolving cutter 24 is described by the relationship:

$F = mN^2R$, where $F$ = the centrifugal force exerted on the waste,
$m$ = the mass of the waste forced between cutter teeth,
$N$ = the rotating speed of the shaft, and
$R$ = the cutter radius.

In addition to the centrifugal force acting to move the medical waste outwardly into contact with teeth 30 and teeth 36, the rotation of revolving cutter 24 generates a force acting against air within the interior of housing 10, similar to the blades of a fan. This force further cooperates with centrifugal force to move the medical waste outwardly toward teeth 30 and 36.

As shown in FIG. 1, revolving cutters 24 and stationary cutters 32 preferably extend along substantially the entire length of housing 10. This unique concept facilitates the installation of cutters 24 and 32 by simplifying the alignment and attachment of cutters 24 and 32. This concept minimizes interior surfaces allowing undesired attachment with medical waste material, blocks medical waste material from wrapping around rotating shaft 22, and reduces potential dead spaces within the interior of housing 10 which could permit the undesirable accumulation of medical waste residue. Additionally, this concept provides uniform cutting regions between teeth 30 and 36 which create a consistent distribution of medical waste particles at selected positions within housing 10. Consequently, the comminution of medical waste particles to a selected particle size is easily controlled by the length of housing 10 and the dimensions and orientation of corresponding cutting regions between teeth 30 and 36.

Frictional forces and turbulence in the cutting region between teeth 30 and 36 create drag forces resisting the flow of medical waste residue through housing 10. Because such frictional forces are less toward housing 10 center along longitudinal axis 20, medical waste residue along longitudinal axis 20 will tend move toward discharge 14 at a higher rate than medical waste residue accumulating toward the cutting surfaces between teeth 30 and 36. As previously noted, forces due to centrifugal force and revolving cutter displacement cooperate to mix the lighter and heavier particles of medical waste residue.

To enhance the homogeneous processing of the medical waste residue, to prevent excessive stratification of heavier versus lighter particles in the medical waste residue, and to transport the medical waste residue toward discharge 14, blades 40 mix the medical waste residue within housing 10. Blades 40 mechanically accomplish this result without requiring high speed rotation of shaft 22. Accordingly, a highly efficient shredding apparatus is provided with simple components that avoid the expense and maintenance required by high speed equipment such as vortical cyclones and centrifuges.

Figure 2:
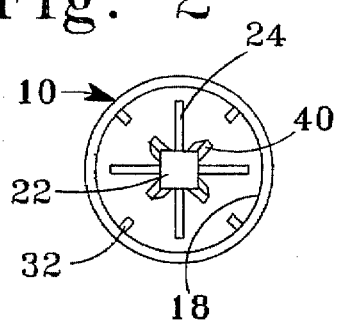
FIG. 2 illustrates an end view for one embodiment of a housing and cutter elements.

FIG. 2 illustrates an end view of housing 10 wherein multiple revolving cutters 24 and blades 40 are attached to shaft 22, and wherein multiple stationary cutters 32 are attached to interior surface 18. The number and orientation of revolving cutters 24 and blades 40 can be selected to balance shaft 22 as shaft 22 rotates within housing 10. In preferred embodiments of the invention, pairs of revolving cutters 24 are attached to opposite sides of shaft 22 to facilitate balancing of shaft 22.

Figure 3:
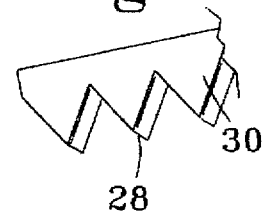
FIG. 3 illustrates a detail view of cutter teeth.

FIG. 3 shows detail for one configuration of teeth 30, wherein revolving cutter 24 comprises a rectangular blade having sawtooth cutting surface 28 for teeth 30. As shown, the sides of teeth 30 are preferably cut ninety degrees relative to the flat, leading surface of revolving cutter 24. In this configuration, teeth 30 are not easily dulled and retain the strength proportional to the thickness of revolving cutter 66. Such thickness can be reduced or increased as desired to achieve a selected rotational mass and strength for revolving cutter 24. Teeth 30 cooperate with intermeshing teeth 36 to cut, shear, shred, tear, mill, grind, pulverize and otherwise reduce the particle size of the medical waste.

Figure 4:
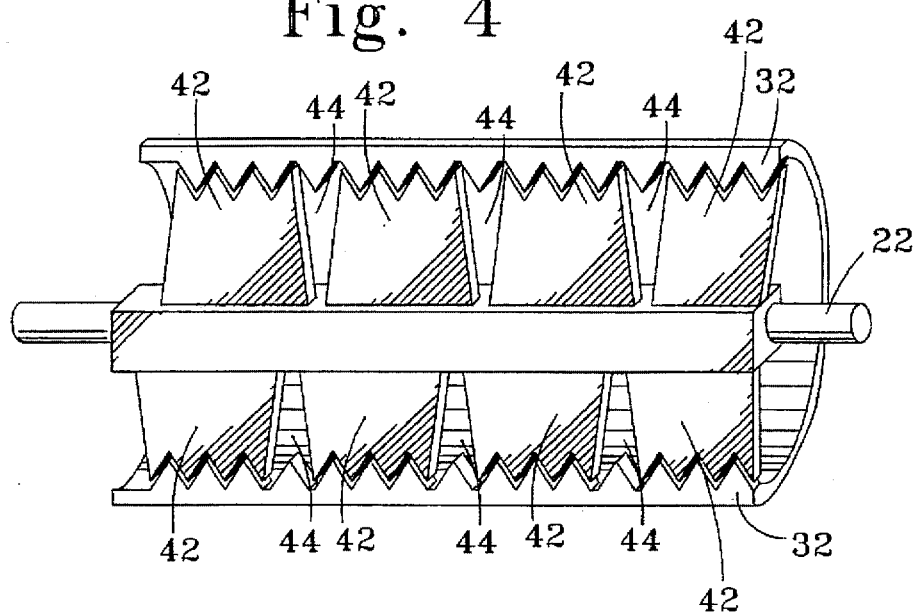
FIG. 4 illustrates a segmented cutter blade.
Figure 5:
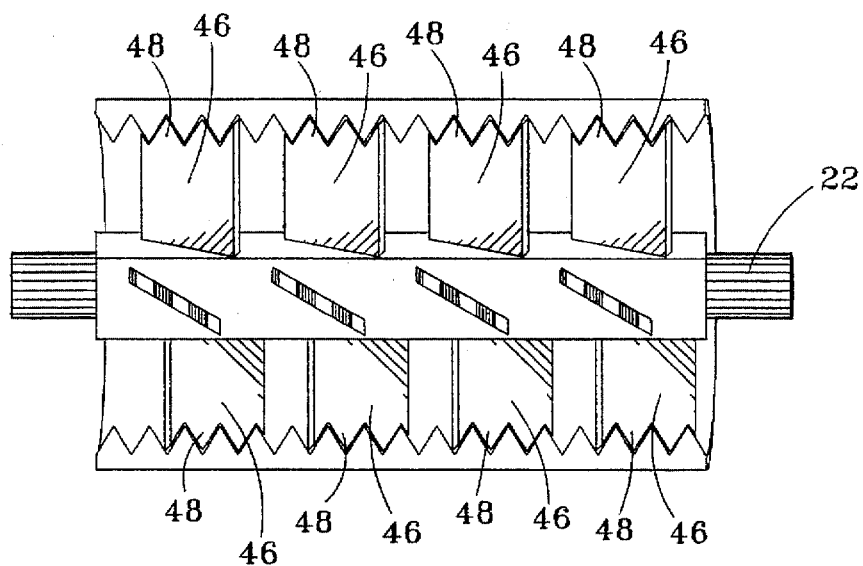
FIG. 5 illustrates a rotatable shaft having angled cutter elements which comminute and transport medical waste.

FIG. 4 illustrates another embodiment of the invention wherein revolving cutters 42 are segmented with openings 44 and do not extend the entire length of housing 10. This embodiment of the invention permits flow of medical waste residue through openings 44 and can enhance mixing action accordingly. As shown in FIG. 5 for an alternative embodiment of the invention, the placement of segmented revolving cutters 46 permits the elimination of separate propellers such as revolving blades. By orienting cutters 46 so that cutter surfaces 48 are at an angle relative to longitudinal axis 20, cutters 46 provide the simultaneous functions of a propeller or blade for transporting the medical waste residue toward discharge 14 while reducing the unconsolidated medical waste into medical waste residue.

Figure 6:
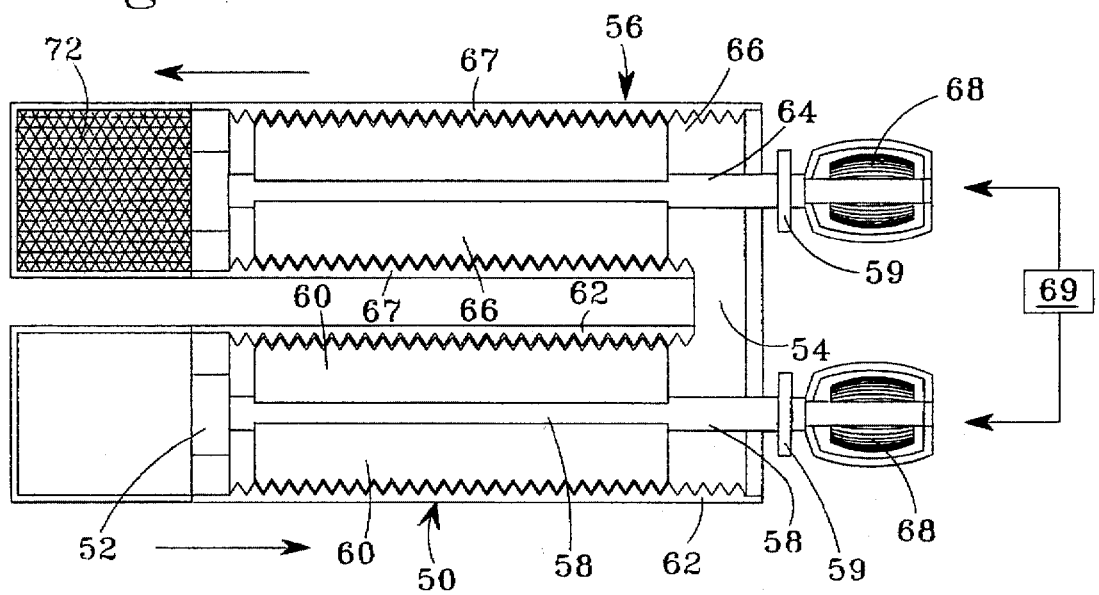
FIG. 6 illustrates a system having first and second stage cutters.

FIG. 6 illustrates another embodiment of the invention, wherein multiple housings can be combined to progressively reduce unconsolidated medical waste into medical waste residue. First stage cutter 50 receives unconsolidated medical waste in inlet 52 and provides a first cut which reduces such unconsolidated medical waste to a selected particle size. Such medical waste is then discharged into inlet 54 of second stage cutter 56 and is further reduced by second stage cutter 56 to complete the processing of unconsolidated medical waste into medical waste residue. First stage cutter 50 has shaft 58, flywheel 59, revolving cutters 60 attached to shaft 58, and stationary cutters 62. Second stage cutter 56 has shaft 64, flywheel 59, revolving cutters 66, and stationary cutters 67. Motors 68 drive shafts 58 and 64. Flywheel provides angular momentum which facilitates the rotation of shafts 58 and 64 during fluctuations in the cutting resistance created by the waste material or due to current fluctuations in motors 68. By positioning first stage cutter 50 and second stage cutter 56 in a substantially horizontal orientation, the system does not rely on gravity to pull the medical waste through the system as previously described. The combination of first stage cutter 50 and second stage cutter 56 permits an efficient combination of cutters having different configurations for sequentially reducing unconsolidated medical waste into medical waste residue.

Various features can be incorporated into the design of the invention, including control panel 69, for monitoring and for adjusting the operation of the working components such as motors 68. In one representative example of a system, control panel 69 can operate the rotation of shaft 58 at rotational speeds between twenty and fifty revolutions per minute to perform an initial cut on the unconsolidated medical waste, and can operate the rotation of shaft 64 at between 300 and 400 revolutions per minute to complete processing of the medical waste into medical waste residue. Control panel 69 can reverse the direction of electric motors and other moving components to dislodge any medical waste that becomes trapped within the system.

The system uniquely permits a low profile which facilitates the entry of unconsolidated medical waste into the system at inlet 54. The unconsolidated medical material can be introduced near ground level and does not have to be elevated or otherwise conveyed prior to entry into the system. Such system can be operated between floors of buildings and does not require the overhead space typically provided by warehouse facilities or outside spaces. Accordingly, the present invention is adaptable to the interior spaces of buildings, and can be positioned near the origin point of the unconsolidated medical waste. This unique feature reduces the transportation and handling of the unconsolidated medical waste and the risks associated with such transportation and handling.

Screen 72 can be positioned downstream of second stage cutter 56 to prevent any possibility of oversized material from exiting the system. If desired, any oversized particles removed by screen 72 can be rerouted manually or automatically into inlet 52 or inlet 54. Screen 72 will also function with other embodiments of housings and cutters disclosed herein.

Figure 7:
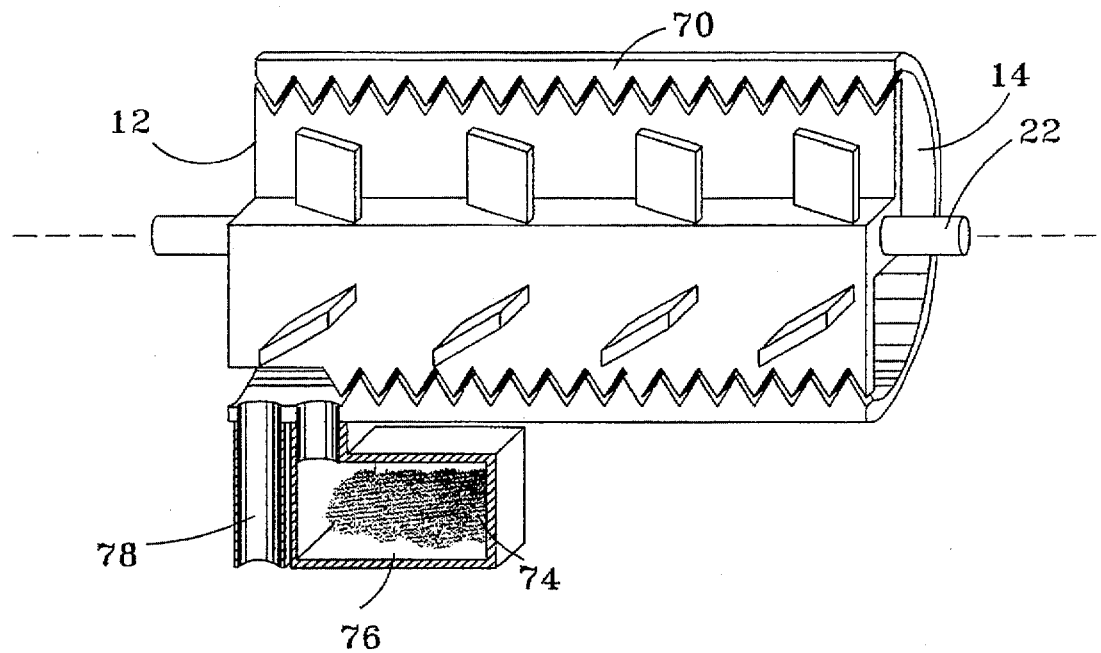
FIG. 7 illustrates components for introducing sterilant into contact with the medical waste.

FIG. 7 illustrates another embodiment of the invention wherein cutter housing 70 reduces unconsolidated medical waste into medical waste residue as previously described. To sterilize the medical waste residue, sterilant 74 is introduced into housing 70 so that sterilant 74 combines with the medical waste. Sterilant 74 can comprise a liquid, gas, powder or other material suitable for combining with and for sterilizing, disinfecting or sanitizing the medical waste. In one embodiment of the invention, a disinfectant or sterilant 74 preferably destroys pathogens in the medical waste at of rate of six log kill or higher. Depending on the physical composition, sterilant 74 can be introduced into the interior of housing 70 through an injector nozzle, port, mechanical spreader, screw conveyor or other suitable dispenser generally shown as 76. In a preferred embodiment of the invention, a sterilant 74 comprises a dry material for absorbing and desiccating fluids in the medical waste, and for stabilizing heavy metals in the medical waste.

Sterilant 74 is preferably introduced into contact with the unconsolidated medical waste at an early stage within housing 70 to maximize the mixing of sterilant 74 with the medical waste particles as the medical waste residue is comminuted. If a dry material is used for sterilant 74, nozzle 78 can spray water or other fluids onto sterilant 74 in the interior of housing 70 to activate dry sterilant 74. In this embodiment of the invention described for FIG. 7, the medical waste residue discharged from housing 70 is nonhazardous to biological organisms, thereby simplifying the handling, transportation and storage of the non-infectious medical waste residue. The sterilant features described for FIG. 7 can be adapted to other embodiments.

Figure 8:
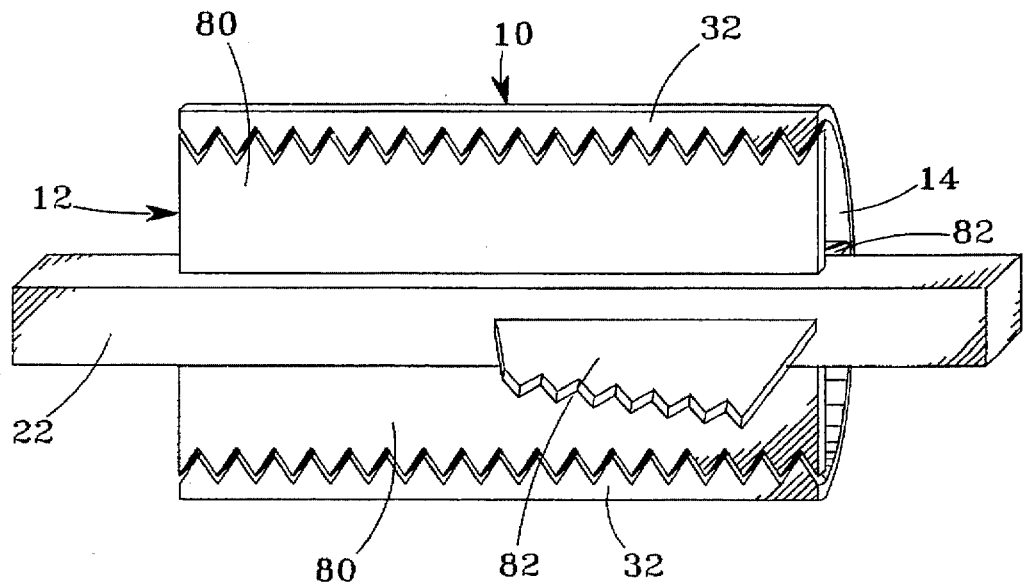
FIG. 8 illustrates one embodiment of the invention having a combination of full length cutting blades and partial length cutting blades.

FIG. 8 illustrates another embodiment of the invention wherein stationary cutters 32 are attached to housing 10 and shaft 22 revolves within housing 10. Full length revolving cutters 80 and partial length revolving cutters 82 are attached to shaft 22. Partial length revolving cutter 82 has beveled surface 84 for reducing the opportunity of medical waste attachment. As unconsolidated medical waste enters inlet 12, full length revolving cutters 32 make the preliminary cut. As the medical waste is transported through housing 10, partial length revolving cutters 82 increase the number of cuts made per length of housing 10.

The teeth illustrated as teeth 30 and 36 can be modified to accomplish different objectives. For example, the size of teeth 30 on a particular cutter can change along the longitudinal axis of the cutter. Small teeth can be used to initiate the first cut, and larger teeth can be attached to the same cutter to cut the waste material further downstream of the housing inlet. This order could be reversed to accomplish different cutting action, and the teeth could be shaped as a combination of large and small teeth to accomplish a desired cutting action.

The present invention furnishes an apparatus capable of efficiently processing a large volume of unconsolidated medical waste into medical waste residue. The unconsolidated medical waste is physically destroyed, reduced to selected particle sizes, and can be sterilized in the same operation. Notably, the invention reduces the unconsolidated medical waste to particle sizes sufficiently small and having a homogeneous appearance so that the medical waste is not recognizable as to its source.

The invention accomplishes this result with minimal moving parts requiring little maintenance. Although the invention provides a unique system for processing medical waste on a continuous flow basis, the medical waste could also be treated on a batch basis to control the treatment time of contact between sterilant 72 and the medical waste. All elements in the system can be contained to prevent the release of untreated contaminants into the environment, and HEPA filters can treat air released from the system interior.

Although the invention has been described in terms of certain preferred embodiments, it will be apparent to those of ordinary skill in the art that modifications and improvements can be made to the inventive concepts herein without departing from the scope of the invention. The embodiments shown herein are merely illustrative of the inventive concepts and should not be interpreted as limiting the scope of the invention.

What is claimed is:

1. An apparatus for converting unconsolidated medical waste into a sterilant disinfected medical waste residue, comprising:

a housing having an inlet for receiving medical waste and having an interior defined by an interior surface;

a dispenser for introducing the sterilant into contact with the medical waste within said housing interior;

a rotatable shaft within said housing, wherein said shaft has a substantially horizontal longitudinal axis;

a revolving cutter having a base attached to said shaft and having a cutting surface radially outward from said shaft, wherein said revolving cutter has a longitudinal axis parallel to said shaft longitudinal axis, and wherein said revolving cutter has a plurality of teeth on said cutting surface which revolve about the longitudinal axis of said rotatable shaft;

a stationary cutter proximate to said housing interior surface, wherein said stationary cutter includes a plurality of teeth on a cutting surface for engagement with the teeth of said revolving cutter to reduce medical waste into medical waste residue;

an outlet for permitting the discharge of the medical waste residue from said housing interior; and a discontinuous propeller for moving the medical waste residue toward said outlet.

2. An apparatus as recited in claim 1, wherein the sterilant comprises a liquid activated powder.

3. An apparatus as recited in claim 1, wherein said revolving cutter is generally shaped as a planar blade.

4. An apparatus as recited in claim 1, further comprising at least two revolving cutters attached to said rotatable shaft and at least two stationary cutters engaged with said housing interior surface.

5. An apparatus as recited in claim 1, wherein said stationary cutter is attached to said housing interior surface.

6. An apparatus as recited in claim 1, wherein said revolving cutter and said stationary cutter substantially extend along the entire length of said rotatable shaft within said housing interior.

7. An apparatus as recited in claim 6, further comprising a partial length revolving cutter attached to said shaft.

8. An apparatus as recited in claim 1, further comprising a first stage cutter for reducing the unconsolidated medical waste and for transporting the reduced medical waste into said housing inlet.

9. An apparatus as recited in claim 1, wherein said propeller comprises a plurality of vanes each have a base attached to said rotatable shaft, and wherein each vane has a distal end extending radially outwardly from said rotatable shaft.

10. An apparatus as recited in claim 1, wherein said revolving cutter and said propeller comprise the same element.

11. An apparatus for converting unconsolidated medical waste into a powder sterilant disinfected medical waste residue, comprising:

a first stage cutter for reducing said unconsolidated medical waste into medical waste residue;

a housing having an inlet for receiving the reduced medical waste from said first stage cutter, and further having an interior volume defined by an interior surface;

a rotatable shaft within said housing interior volume, wherein said shaft has a substantially horizontal axis;

a revolving cutter having a base attached to said shaft and having a cutting surface radially outward from said shaft, wherein said revolving cutter has a longitudinal axis parallel to said shaft longitudinal axis, and wherein said revolving cutter has a plurality of teeth on said cutting surface which revolve about the longitudinal axis of said rotatable shaft;

a stationary cutter attached to said housing interior surface, wherein said stationary cutter includes a plurality of teeth on a cutting surface for engagement with the teeth of said revolving cutter to further reduce the medical waste residue processed by said first stage cutter;

a dispenser for introducing the powder sterilant into contact with the medical waste within said first stage cutter;

an outlet for permitting the discharge of the processed medical waste residue from said housing interior volume; and a vane engaged with said rotatable shaft for moving the medical waste toward said outlet.

12. An apparatus as recited in claim 11, further comprising at least two revolving cutters attached to said rotatable shaft and at least two stationary cutters attached to said housing interior surface.

13. An apparatus as recited in claim 11, wherein said first stage cutter includes a rotatable shaft having a substantially horizontal longitudinal axis, a revolving cutter attached to said shaft, a stationary cutter engaged with said revolving cutter for reducing the unconsolidated medical waste, and a propeller for moving the medical waste toward said housing inlet.

14. An apparatus as recited in claim 11, wherein said revolving cutter and said stationary cutter substantially extend along the entire length of said rotatable shaft within said housing interior.

15. An apparatus as recited in claim 14, further comprising a partial length revolving cutter attached to said shaft.

16. An apparatus as recited in claim 15, wherein said teeth on said revolving cutter and on said stationary cutter comprise sawtooth teeth having serration surfaces at a ninety degree angle relative to said planar side surfaces.

17. An apparatus as recited in claim 11, wherein said revolving cutter and said stationary cutter comprise rectangular blades having planar side surfaces.

18. An apparatus as recited in claim 11, further comprising a screen for receiving the processed medical waste residue from said outlet and for separating the processed medical waste residue into at least two size classifications.

* * * * *